United States Patent
Stöver et al.

(10) Patent No.: US 7,786,342 B2
(45) Date of Patent: *Aug. 31, 2010

(54) **DOUBLE FLOWER *CALIBRACHOA* BREEDING METHODS AND PLANTS PRODUCED THEREFROM**

(75) Inventors: Anita Stöver, Stuttgart (DE); Andrea Dohm, Stuttgart (DE); Ulrich Sander, Stuttgart (DE); Nils Klemm, Stuttgart (DE)

(73) Assignee: Klemm + Sohn GmbH & Co., Stuttgart (DE)

( * ) Notice: Subject to any disclaimer, the term of this patent is extended or adjusted under 35 U.S.C. 154(b) by 384 days.

This patent is subject to a terminal disclaimer.

(21) Appl. No.: 11/522,499

(22) Filed: Sep. 14, 2006

(65) Prior Publication Data

US 2008/0072339 A1    Mar. 20, 2008

(51) Int. Cl.
*A01H 5/00* (2006.01)
*A01H 5/10* (2006.01)
*A01H 1/00* (2006.01)
*A01H 1/02* (2006.01)

(52) U.S. Cl. .............. 800/260; 800/298; 800/295; 800/317; 435/468; 435/430; 435/430.1

(58) Field of Classification Search .............. None
See application file for complete search history.

(56) References Cited

U.S. PATENT DOCUMENTS

PP15,837 P2 * 7/2005 Westhoff

* cited by examiner

*Primary Examiner*—Medina A Ibrahim
(74) *Attorney, Agent, or Firm*—Jondle & Associates, P.C.

(57) ABSTRACT

A method for breeding double flower *Calibrachoa* sp. plants using controlled crosses of selected parent plants is disclosed. The invention additionally relates to methods for breeding double flower *Calibrachoa* plants using anther culture and induced mutation techniques. Finally, the invention relates to new *Calibrachoa* plants produced by the described methods and characterized by their unique double flowers.

12 Claims, 15 Drawing Sheets
(1 of 15 Drawing Sheet(s) Filed in Color)

ized in the present invention relates to methods for breeding double flower *Calibrachoa* plants using controlled crosses of selected parent plants. More specifically, the invention relates to methods for breeding double flower *Calibrachoa* plants using interspecific hybridisation, anther culture techniques, and induced mutation. Finally, the invention relates to new *Calibrachoa* plants produced by the described methods and characterized by their unique double flowers.

DOUBLE FLOWER *CALIBRACHOA* BREEDING METHODS AND PLANTS PRODUCED THEREFROM

CROSS-REFERENCE TO RELATED APPLICATIONS

This application claims priority to U.S. Plant Pat. No. 18,694, which was filed on Jun. 23, 2006 and issued on Apr. 1, 2008.

BACKGROUND OF THE INVENTION

The genus *Calibrachoa* was introduced as a bedding plant in the early 1990s. Since 1996, breeders at Klemm & Sohn GmbH & Co. ("Klemm"), a plant breeding company located in Stuttgart, Germany, have conducted a *Calibrachoa* breeding program. The first varieties developed in the breeding program were introduced onto the US market in 2000, and plant patent rights were applied for in 2001 for the first time.

The genus *Calibrachoa* is a very close relative of the genus *Petunia*. While the double flower trait had already been established in *Petunia*, no double flowering *Calibrachoa* types had been discovered so far in the Klemm breeding program, or introduced by any third parties. The inventors were successful in developing methods for breeding *Calibrachoa* plants having double flowers, as described in the following specification.

In general, the present invention relates to methods for breeding double flower *Calibrachoa* plants using controlled crosses of selected parent plants. More specifically, the invention relates to methods for breeding double flower *Calibrachoa* plants using interspecific hybridisation, anther culture techniques, and induced mutation. Finally, the invention relates to new *Calibrachoa* plants produced by the described methods and characterized by their unique double flowers.

DESCRIPTION OF RELATED ART

The science of carrying out controlled crosses to obtain new sexually produced plant varieties is well established, as are breeding programs that produce new *Calibrachoa* species using Mendelian techniques. Numerous *Calibrachoa* species are known, many of which are the subject of U.S. plant patents. However, all previously known *Calibrachoa* varieties of which the inventors are aware exhibit flowers having five petals per flower (referred to herein as "single flowers"), while the plants produced by the methods described herein exhibit "double" flowers, or flowers having more than the five petals typical of *Calibrachoa* species. The inventors are not aware of any other breeding method or breeding program that has successfully produced double flower *Calibrachoa* plants.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
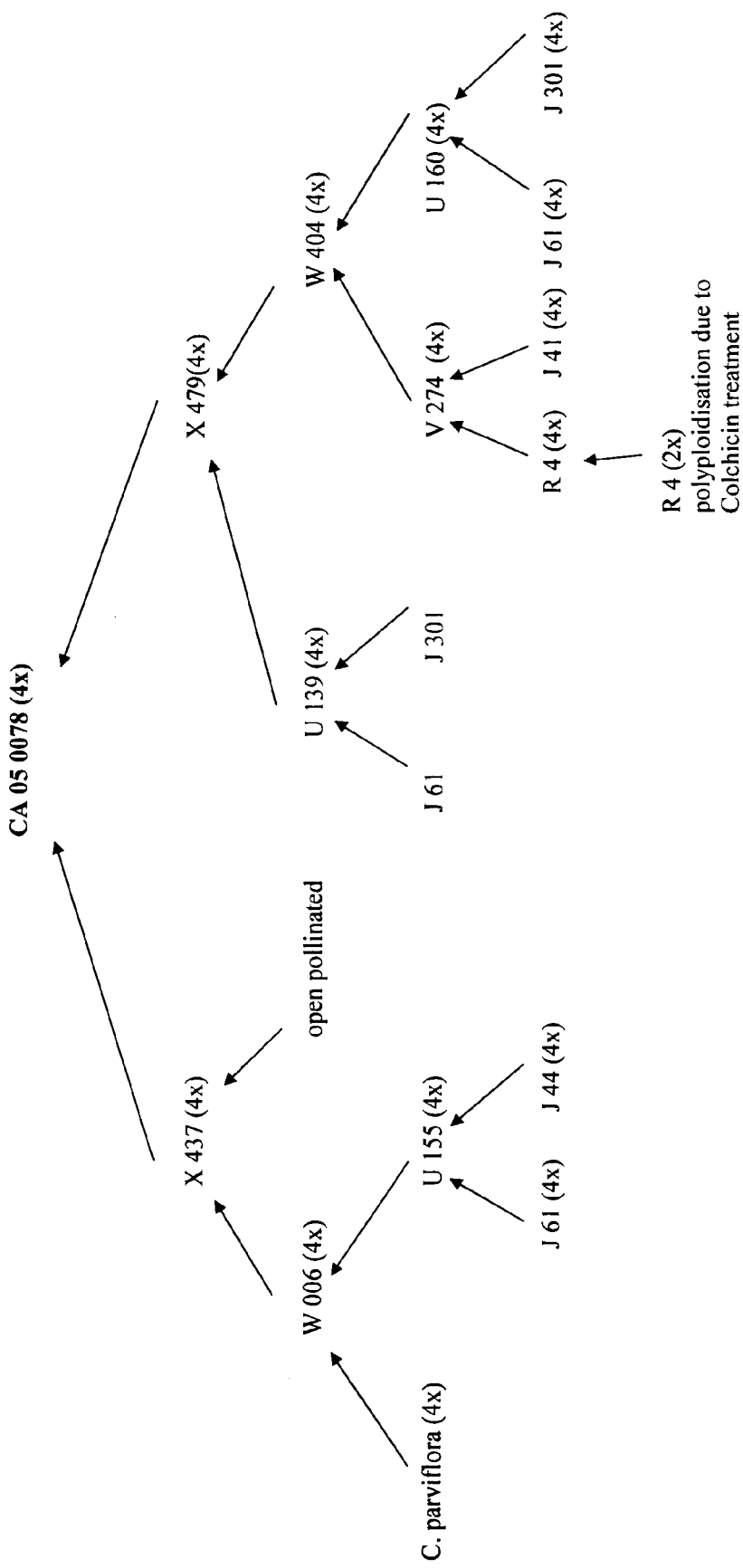
FIG. 1 shows the genealogy of double-type cultivar CA 05 0078 (2n=4x)

According to the present invention, a number of unique process steps are employed to produce *Calibrachoa* genotypes having double flowers, i.e., at least one flower with more than five petals. The additional petals range from a sixth underdeveloped petaloid to a plurality of additional fully developed petals or petaloids. Methods including interspecific hybridization techniques, anther culture techniques, and induced mutation are each discussed in turn.

Interspecific Hybridization to Induce Double Flowering Types Within the Genus *Calibrachoa*:

According to the breeding method of the present invention, a first *Calibrachoa* plant having one or more double-type flowers, or a *Calibrachoa* plant with single-type flowers having the double flowering trait in its genetic background, is used as a source of double-type genes in a breeding program having the goal of producing new double-flowering *Calibrachoa* varieties. The *Calibrachoa* source population may be the result of an intraspecific cross or from interspecific hybridisation comprising more than one species within the *Calibrachoa* genus. The first *Calibrachoa* plant selected from the source population is crossed with a second single-flower or double-flower *Calibrachoa* plant. The respective progenies of the crosses are scored for the double-type phenotype.

It is expected that any selected double-type *Calibrachoa* cultivar can be propagated commercially through asexual propagation. All double-type cultivars thus far tested have been found to be stable through asexual propagation. Cuttings for asexual propagation can be taken at any time of the year and no special hormones or soil mixtures are used. It is also expected that *Calibrachoa* double-type cultivars can be produced as progeny from sexual crosses and sold as seed.

In the breeding program maintained by the inventor, plants to be crossed are usually grown in 3 liter pots containing a mixture of porous coco peat and clay. The plants are grown at 16° C. to 20° C. day and night temperature. They are watered with a solution containing 20% nitrogen, 5% potassium, 10% phosphorus and 2% magnesia.

Crosses can be made from May to September under European light conditions. The highest success rate, however, is observed during cooler summer months, because in warmer temperatures, particularly above 33° C., the viability of the pollen decreases rapidly. The flowers to be used as the female parent need not be emasculated because of the gametophytic self-incompatibility system within *Calibrachoa*. Pollen picked from flowers that are to be used as the male parent is used to pollinate mature stigmas of the female parent. Within the same crossing combination one to 3 flowers are pollinated. A tag is placed on each pollinated flower, showing the date of pollination and the identity of male and female parents.

Ripening of the seed pods occurs 6 to 9 weeks after pollination, depending on the environmental conditions. Cool and cloudy weather increases the time required for ripening of the seed pods. The collected seeds are cleaned by hand, separated from the pod chaff and stored in greaseproof paper bags. The seeds should be stored at room temperature not more than 8 months, because seed viability decreases after long storage.

The *Calibrachoa* population of interbreeding species included: *Calibrachoa calycina, C. parensis, C. ericifolia, C. ovalifolia, C. heterophylla, C. humilis, C. parviflora, C. sellowiana, C. spathulata, C. elegans, C. caesia, C. micrantha, C. sendtneriana, C. linoides, C. excellens, C. eglandulata, C. dusenii, C. rupestris, C. thymifolia, C. eglandulata, C. micrantha, C. ovalifolia,* and *C. paranensis*. It is anticipated that other *Calibrachoa* species will be identified in the future, and that those species could be similarly incorporated into an interspecific breeding program.

After carrying out crosses of *Calibrachoa* plants as described above and obtaining 17,500 first generation seedlings, the inventors identified a total of 14 plants having one or more flowers with more than 5 petals per flower. Of these first generation plants, 13 plants (W 001, W 003, W 004, W 005, W 006, W 007, W 008, W 009, W 010, W 011, W 012, W 013 and W 014; Ploidy level 2n=4x) resulted from the cross 'U155'
Ploidy level: $2n = 4x$ × *Calibrachoa parviflora*
(unpatented Klemm *Calibrachoa* cultivar) Ploidy level: $2n = 4x$ In this cross, the male parent, a tetraploid *Calibrachoa parviflora*, had small white flowers, and did not show more than 5 petals per flower. Female parent 'U 155' likewise did not exhibit more than 5 petals per flower. However, the first generation progeny included double flowering plants. Selections W 001, W 003, W 004, W 005, W 006, W 007, W 008, W 009, W 010, W 011, W 012, W 013 and W 014, selected from among the first generation progeny, produce light pink flowers having a first row of 5 petals, and usually a second row having 1 to 3 petals. About 20% to 60% of the flowers of these selections had more than 5 petals per flower.

The other first generation seedling, W 002, was the result of the cross

S3('Cherry')
Ploidy level: $2n = 2x$ × *Calibrachoa parviflora*
(unpatented Klemm *Calibrachoa* cultivar) Ploidy level: $2n = 2x$ S 3 ('Cherry') is described in European Community Plant Breeders Right No. EU 10704 granted Feb. 24, 2003. The male parent of W 002 was a diploid *Calibrachoa parviflora* having lavender colored flowers with not more than five petals per flower. The female parent of W 002 was 'S 3', a diploid selection. Neither parent showed the characteristic of more than 5 petals per flower, but W 002 exhibited the double flowering trait sought by the inventors. Approximately 5% to 30% of the flowers produced by W 002 had a single, underdeveloped, sixth petal.

The breeding program was continued, using W 001 to W 014 as breeding material, with the goal of selecting new and unique double-type *Calibrachoa* cultivars with increased doubleness. This goal was accomplished by crossing *Calibrachoa* cultivars selected from the breeding material group W 001 to W 014, with selected *Calibrachoa* cultivars having desireable characteristics, such as a broad range of flower color, different ploidy levels (2n=2x, 3x or 4x), growing habit, branching, etc. The breeding program included intercrossing of siblings (F2) or half-siblings selected from the progeny of the previous crosses, and further included outcrossing to increase genetic diversity, incorporate desirable *Calibrachoa* traits and circumvent inbreeding depression. In addition, some single-type selections were included in these crosses in order to introduce other colors and characteristics into the doubleness breeding program. Twenty-two cross combinations were made in total with the first generation. Only 8 of the 22 cross combinations resulted in seed set, and the total seed yield was very poor, only 106 seeds.

In addition to the controlled crosses described above, open pollination was also carried out. The double-types were grouped at an isolated place and were open pollinated by bumble bees. Better seed yields were obtained by open pollination than were obtained in the controlled crosses. The seeds produced by open pollination were sown, and the resulting seedling populations showed improvement for plant type, habit, flower color and progress in increasing the degree of doubleness per flower or plant.

From the above described crosses of first generation plants, second generation progeny having increased doubleness per flower were selected and incorporated into the ongoing breeding program.

Once again, crosses were made among the selections from the second generation plants, to increase the occurrence of plants with a greater quantity of petals per flower. Second generation selections were crossed with first generation selections, as well as with different *Calibrachoa* varieties having characteristics such as a broad range of flower color, different ploidy levels, growing habit, branching, etc. The breeding program also included sib- and half-sib crossing, backcrossing, and outcrossing with other *Calibrachoa* species to increase genetic diversity, incorporate desirable *Calibrachoa* traits, and circumvent inbreeding depression. The harvested seeds were sown to produce third generation progeny, which were screened for increased number of flower petals, as well as for desirable characteristics relating to growing habit, branching, flower colors, etc. 850 seedlings out of a total of 18,000 third generation seedlings exhibited a genetic background of double-type flowers. The selected progeny again showed a greater quantity of petals per flower as well as a greater quantity of double flowers per plant.

Crosses were made among the selections of the third generation exhibiting double-type flowers, to increase the occurrence of plants with a greater quantity of petals per flower. Third generation selections were crossed with first and second generation selections, as well as with different *Calibrachoa* varieties having characteristics such as a broad range of flower color, different ploidy levels, growing habit, branching, etc. The breeding program also included sib- and half-sibcrossing, backcrossing, and outcrossing with other *Calibrachoa* species to increase genetic diversity, incorporate desirable *Calibrachoa* traits, and circumvent inbreeding depression. Progeny from these crosses again showed an increased number of petals per flower. Nearly 50% of the seedling progeny showed flowers with more than 5 petals. 80% of the double flower types exhibited approximately 8 to 10 petals per flower. This year the fourth generation is being evaluated within the seedling progeny.

Figure 2:
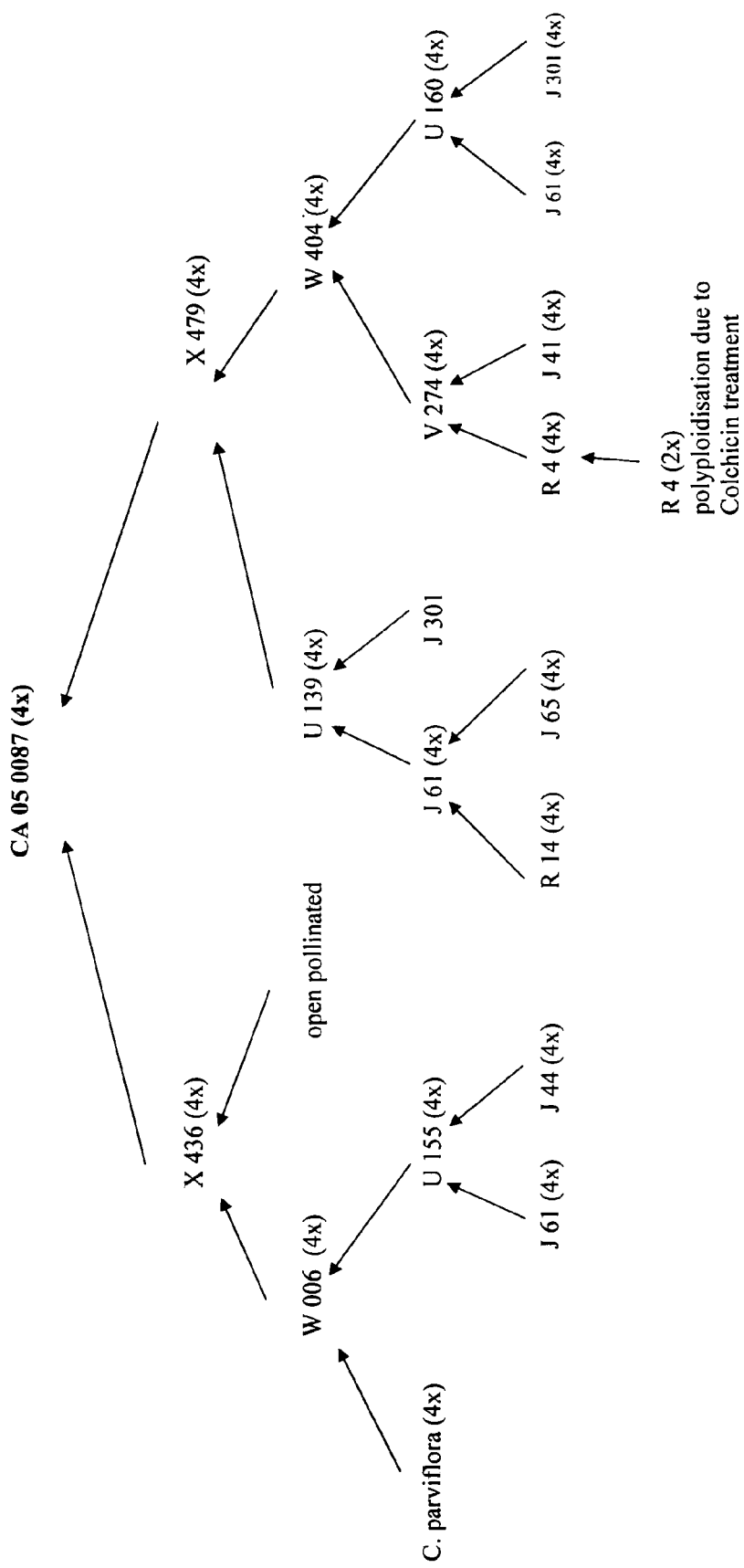
FIG. 2 shows the genealogy of double-type cultivar CA 05 0087 (2n=4x)
Figure 3:
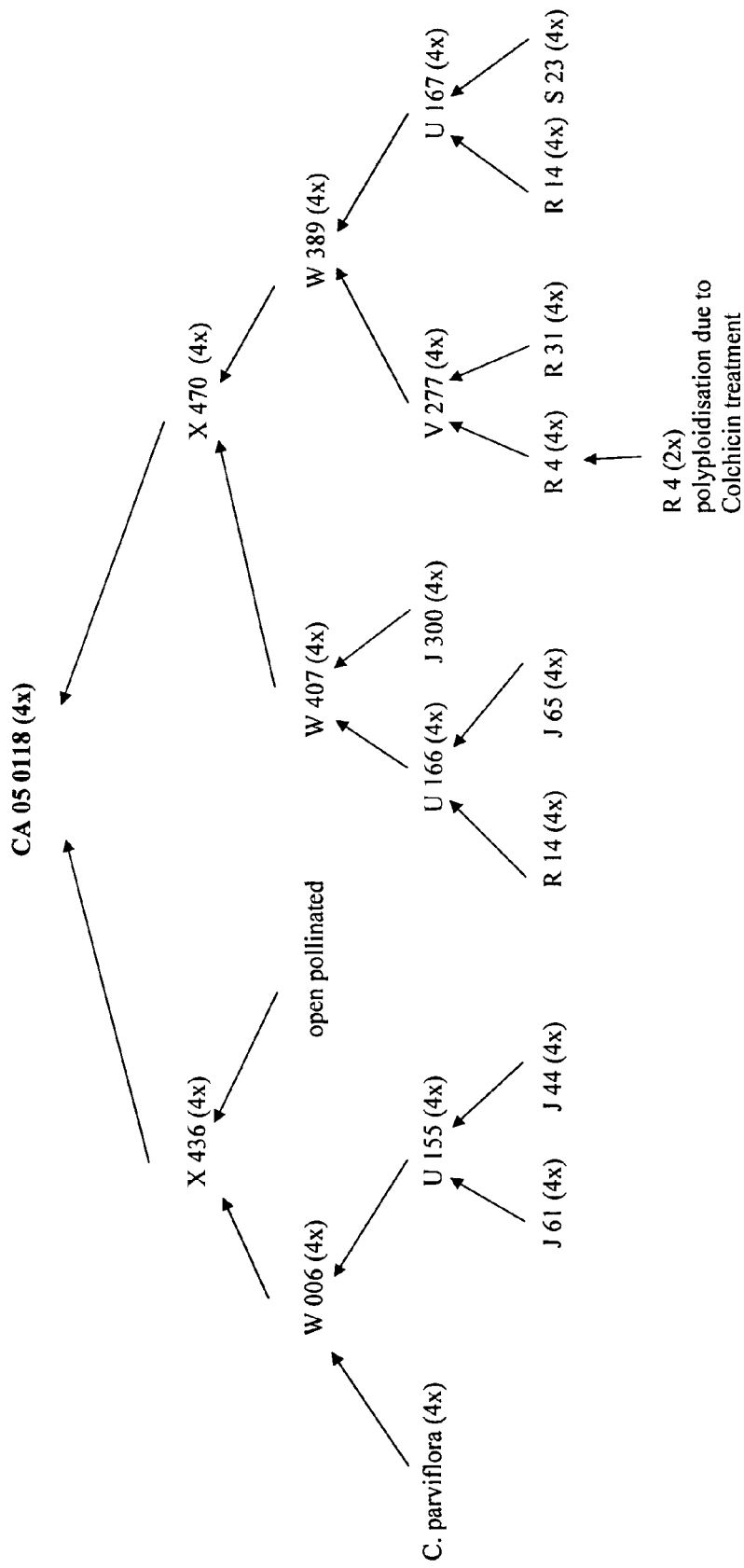
FIG. 3 shows the genealogy of double-type cultivar CA 05 0118 (2n=4x)
Figure 4:
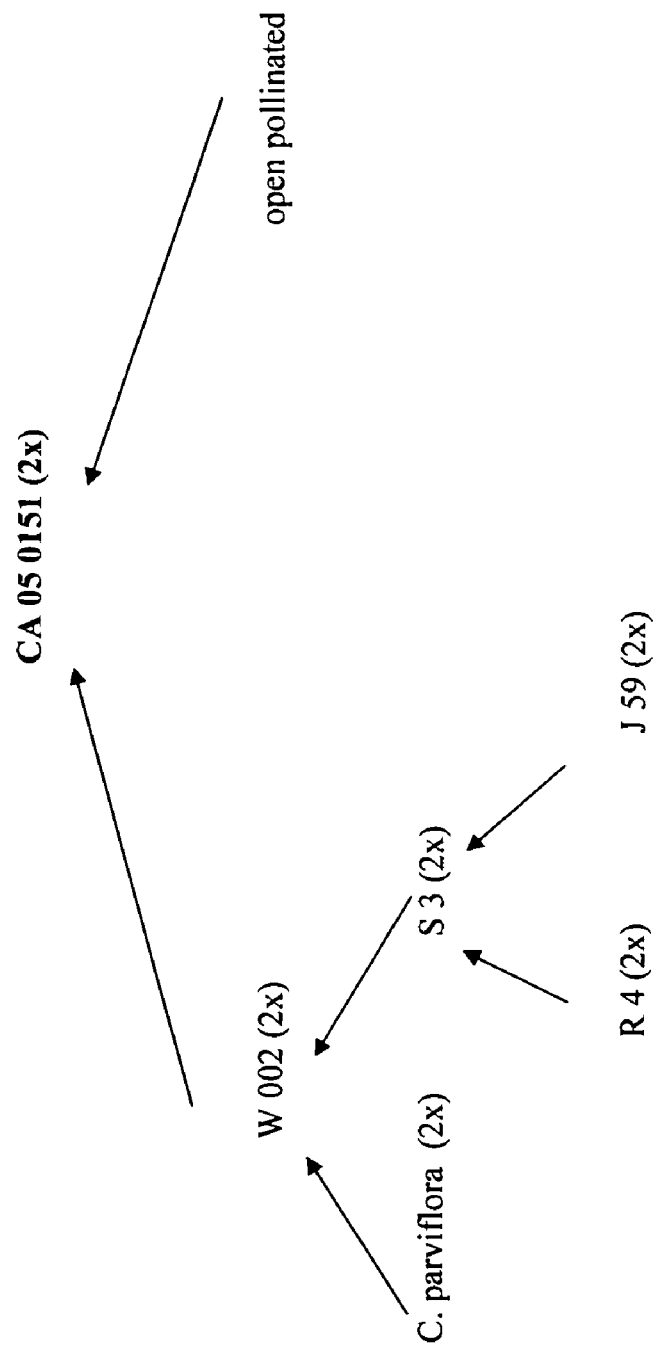
FIG. 4 shows the genealogy of double-type cultivar CA 05 0151 (2n=4x)
Figure 5:
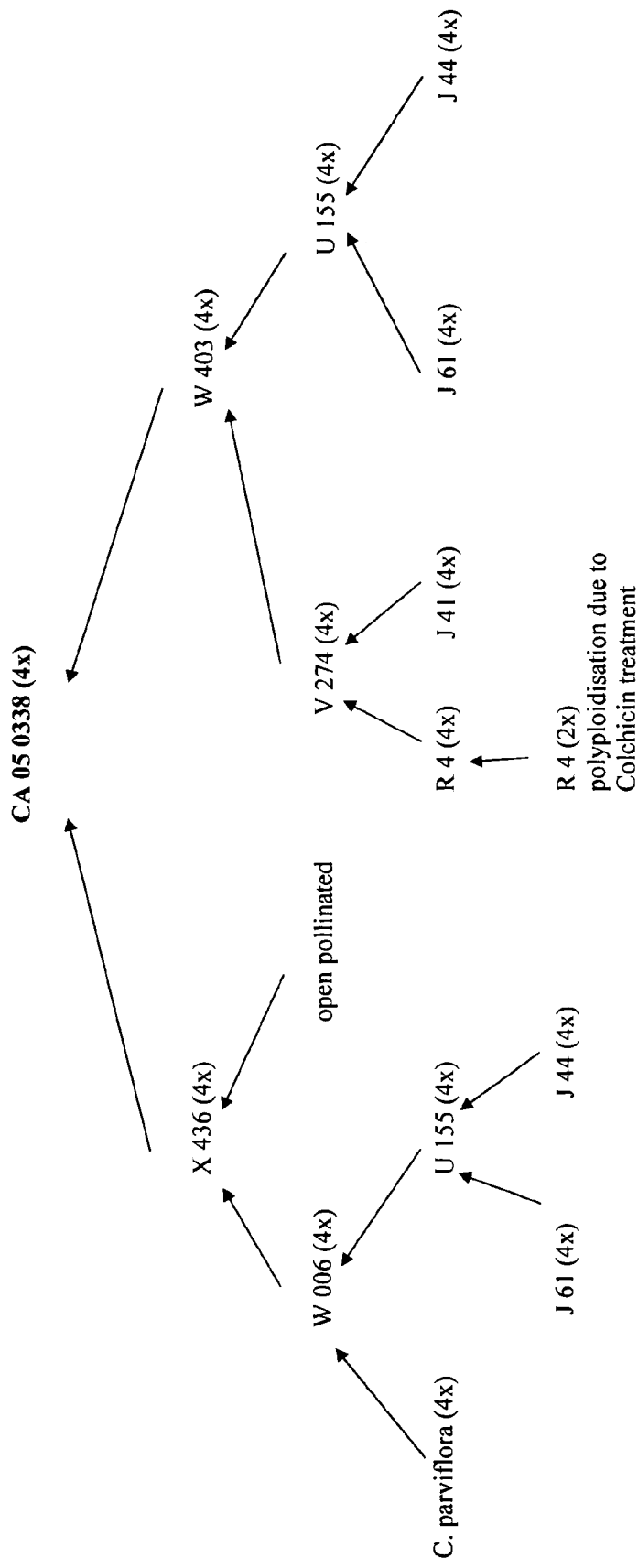
FIG. 5 shows the genealogy of double-type cultivar CA 05 0338 (2n=4x)
Figure 6:
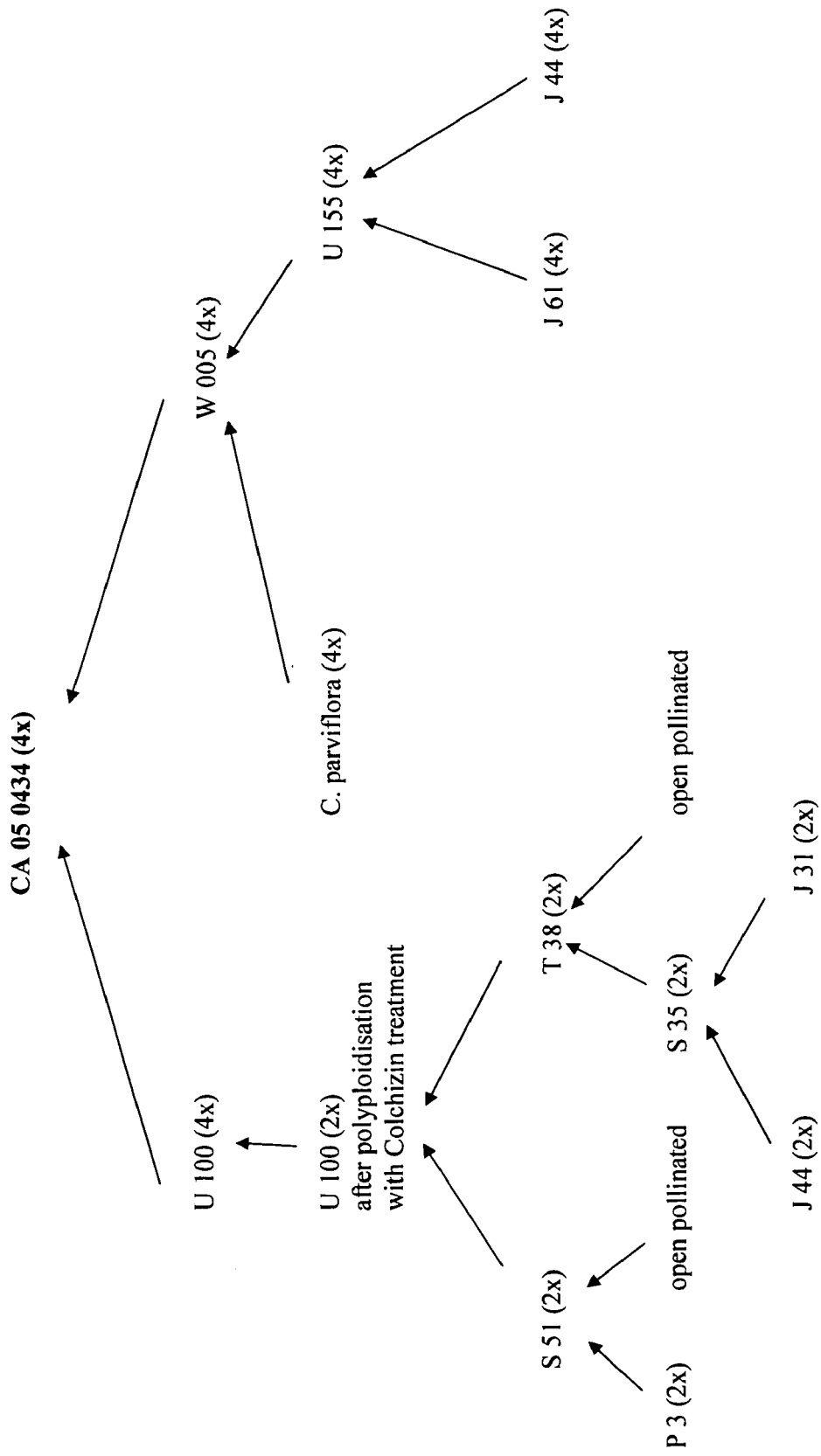
FIG. 6 shows the genealogy of double-type cultivar CA 05 0434 (2n=4x)
Figure 7:
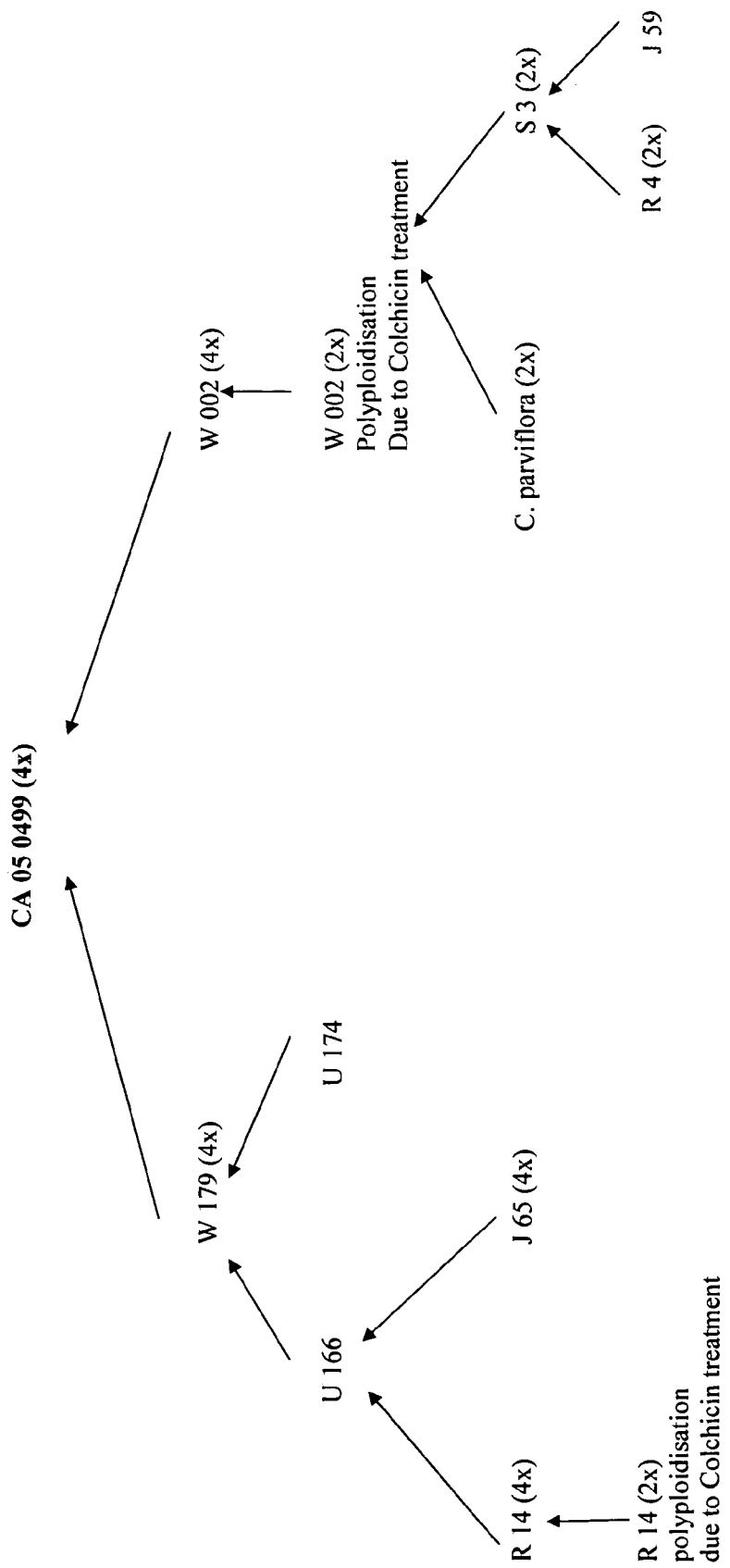
FIG. 7 shows the genealogy of double-type cultivar CA 05 0499 (2n=4x)
Figure 8:
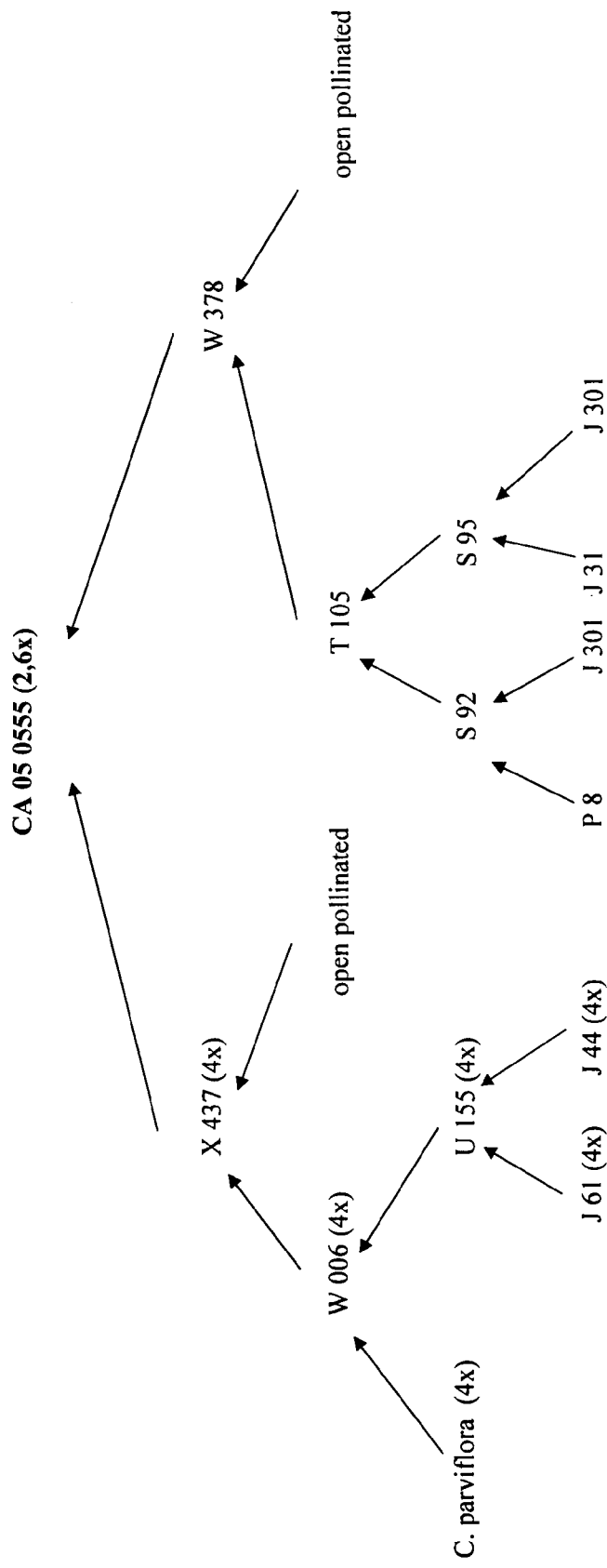
FIG. 8 shows the genealogy of double-type cultivar CA 05 0555 (2n=2.6x)
Figure 9:
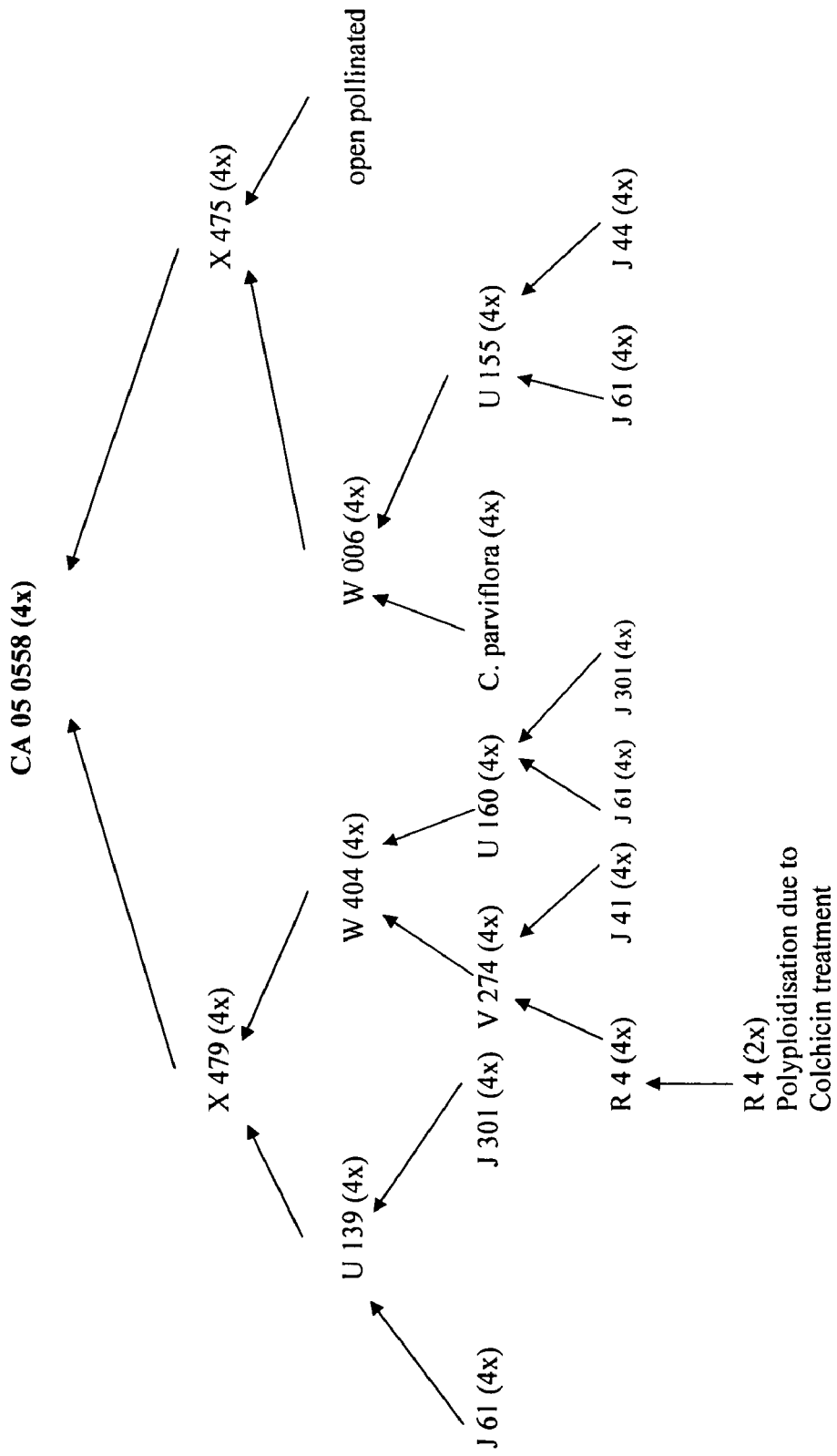
FIG. 9 shows the genealogy of double-type cultivar CA 05 0558 (2n=4x)
Figure 10:
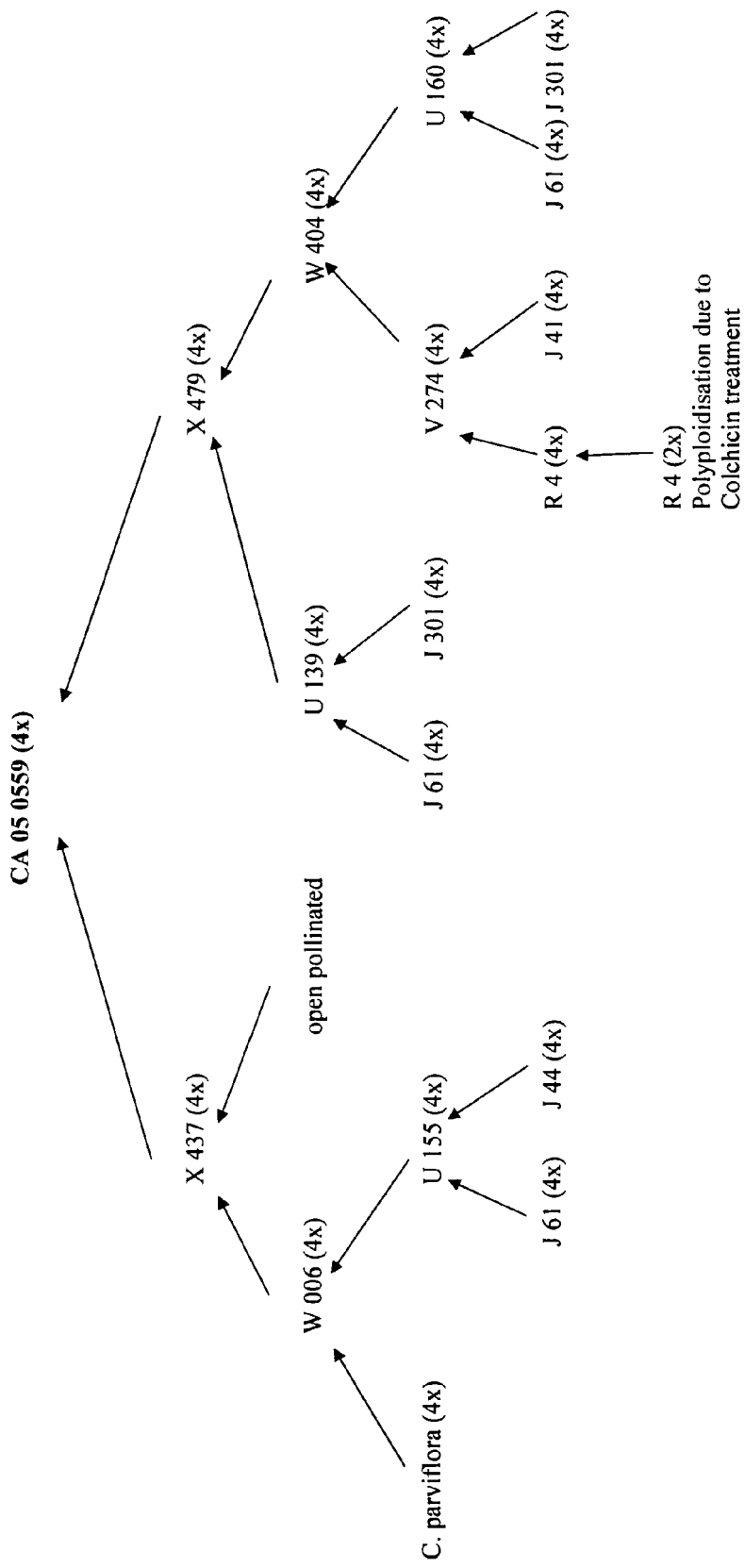
FIG. 10 shows the genealogy of double-type cultivar CA 05 0559 (2n=4x)

The genealogies of third generation double-type cultivars, produced using the breeding method described above, are shown in FIGS. 1 through 10. All crosses were made by the methods described in detail hereinabove. Particular success in obtaining double-flower progeny was achieved in crosses incorporating first generation selections W 002, W 003, W 005 and W 006. Seeds and propagatable plant material of W 002, W 003, W 005 and W 006 are maintained by Klemm & Sohn GmbH & Co., Stuttgart, Germany. A description of the botanical characteristics of W 002, W 003, W 005 and W 006 is provided in Table 1.

Several strategies are available by which doubleness can be successfully fixed within the species *Calibrachoa* and by which this trait can be bred into diverse single-type selections and combined with other desirable *Calibrachoa* characteristics. These strategies include crossing a double-type *Calibrachoa* plant, or a single-type *Calibrachoa* plant with the double flowering trait in its genetic background, with a single- or double-type *Calibrachoa* plant, and selecting progeny exhibiting double flowers. Further crosses can be performed over several generations, including crosses with single- and double-type selections. The crosses can include outcrossing, sib- and half-sib crossing, and back crossing. Plants can be selected for crosses based on their double flowering characteristics, as well as for desirable characteristics such as flower color, branching habit, and others. All crosses can be performed on different ploidy levels (2x, 3x, 4x). From the progeny resulting from each cross, genotypes having one or more flowers with more than 5 petals per flower can be selected. It has been shown that the breeding methods described herein are effective for producing new and distinct *Calibrachoa* plants having double flowers.

Double-flowered *Calibrachoa* selections obtained using the methods described above, including W 002, W 003, W 004, and W 005, and those selections essentially derived therefrom, are considered to be within the scope of the invention. An essentially derived selection is one that: is predominantly derived from the initial selection, or from a selection that is predominantly derived from the initial selection, while retaining the expression of the essential characteristics that result from the genotype or combination of genotypes of the initial selection; is clearly distinguishable from the initial variety; and except for differences that result from the act of derivation, conforms to the initial variety in the expression of the essential characteristics that result from the genotype or combination of genotypes of the initial variety.

TABLE 1

Botanical Characteristics of W 002, W 003, W 005 and W 006

| | W 002 | W 003 | W 005 | W 006 |
|---|---|---|---|---|
| Type | Annual | Annual | Annual | Annual |
| Vigor | Low | Low | Medium | Low |
| Overall Plant Shape | Flat | Flat | Very flat | Flat |
| Growth Habit | Trailing | Trailing | Trailing | Trailing |
| Plant Height | 3 cm | 3.5 cm | 2.5 cm | 4 cm |
| Branching Habit | Poor | Poor | Medium | Low to medium |
| Area of Spread | 16 cm | 17 cm | 24 cm | 19 cm |
| Growth Rate | Low | Low | High | Medium |
| Number of Lateral Branches | 2 | 3 | 5 to 6 | 4 to 5 |
| Lateral Branch Length | 8 cm | 8 cm | 12 cm | 9 cm |
| Leaf Shape | Lanceolate to elliptic | Lanceolate to elliptic | Lanceolate to elliptic | Lanceolate to elliptic |
| Shape of Leaf Tip | Acute | Acute | Broad acute | Broad acute |
| Shape of Leaf Base | Attenuated | Attenuated | Attenuated | Attenuated |
| Flower Arrangement | Single | Single | Single | Single |
| Inflorescence Type | Single | Single | Single | Single |
| Number of Flowers per Inflorescence | 1 | 1 | 1 | 1 |
| Flower Type | Semi-double | Semi-double | Semi-double | Semi-double |
| Amount of Petals | 5 petals and 1 petaloid | More than 5, usually 6 to 7[1] | More than 5, usually 6 to 8[1] | More than 5, usually 6 to 8[1] |
| Fragrance | None | None | None | None |
| Flower Bud Shape | Irregular-oblong | Irregular-oblong | Irregular-oblong | Irregular-oblong |
| Number of Petaloids | Usually 1[1] | Usually 0 to 2[1] | Usually 0 to 2[1] | Usually 0 to 2[1] |
| Petaloid Shape | Lanceolate | Lanceolate | Lanceolate | Lanceolate |
| Petaloid Margin | Entire | Entire | Entire | Entire |
| Petal Color (fully open, upper side)[2] | Red-purple 67A | Red-purple 68C | Red-purple 68C | Red-purple 68C |
| Petaloid Color | Red-purple 67A | Red-purple 68C | Red-purple 68C | Red-purple 68C |

[1]Not stable during hot season
[2]Color descriptions are taken from the RHS Colour Chart, The Royal Horticultural Society, London.

Use of Anther Culture Techniques to Reduce Ploidy:

Most of the double flowering *Calibrachoa* types used in the Klemm breeding program were at the tetraploid level. All traits inherited by recessive genes can be established and be made visible faster in diploid populations than in tetraploid populations. Due to the fact that most of the *Calibrachoa* double flowering types are tetraploid, the inventors sought a method to create di-haploid breeding material. To broaden the range of colors in the double flowering *Calibrachoa* types, it was necessary to establish a method to reduce the ploidy level in *Calibrachoa* from 4x (tetraploid) to 2x (diploid).

In the literature, anther culture is described as a technique for establishing haploid or di-haploid plants in certain species. In an embodiment of the invention, new *Calibrachoa* cultivars are created using anther culture techniques. Raquin (1982, 1985) describes a protocol for anther culture in *Petunia* species, but anther culture techniques have not previously been used within *Calibrachoa*.

According to the invention, anther culture technique was established for *Calibrachoa* plants. Several different *Petunia* and *Calibrachoa* types were integrated into the analyses, with *Petunia* used as a control.

The mother plants, from which the anthers were harvested, were cultivated in the greenhouse in 3 liter pots containing a mixture of porous coco peat and clay. The plants were grown at 16° to 20° C. day and night temperature. They were watered with a solution containing 20% nitrogen, 5% potassium, 10% phosphorus and 2% magnesia.

Flower buds were harvested at the end of mitosis (optimal length of corolla 0.6-1.6 cm). Sepals were eliminated and the flowers were surface-sterilized by immersion for 10 minutes in a 3% solution of potassium hypochlorite supplemented with 0.1% Tween 20. Subsequent to the sterilization the buds were washed two times in sterilized distilled water. Petals and filaments were eliminated before the anthers were placed in 9 cm Petri dishes with starting media (Table 2), and sealed with PVC film.

The starting media for the anthers contained, as taught by Raquin (1982), only half of the original concentration of the macro nutrients of Murashige and Skoog (1962). The starting media further included the micro nutrients from Hellers's medium (1953) without $FeCl_3$, FeEDTA 10-4 M, the vitamins of Morel and Wetmore's medium (1951), 1 g/l meso-inositol, 0.1 mg/l a-naphthalene acetic acid, 1 mg/l benzylaminopurine, 20 g/l glucose, 20 g/l sucrose, and 8 g/l Bacto agar DIFCO. The pH was adjusted to 5.8 before autoclaving 20 min at 121° C. (Table 2).

TABLE 2

Starting media of anther culture (Raquin 1982)

| | mg/l |
|---|---|
| ½ macro nutrients from M&S media: | |
| $NH_4NO_3$ | 825 |
| $KNO_3$ | 950 |
| $CaCl * 2 H_2O$ | 220 |
| $MgSO_4 * 7 H_2O$ | 185 |
| $KH_2PO_4$ | 85 |
| Hellers Micro nutriments: | |
| $MnSO_4 * H_2O$ | 0.08 |
| $ZnSO_4 * 7 H_2O$ | 1.00 |
| $H_3BO_3$ | 50.00 |
| KJ | 0.01 |
| $CuSO_4 * 5 H_2O$ | 0.03 |
| $AlCl_3 * 6 H_2O$ | 0.054 |
| $NiCl_2 * 6 H_2O$ | 0.03 |
| NaFe-EDTA | 37.5 |
| Vitamins: | |
| Inosit (−20° C.) | 1000 |
| Morel Vitamins: | |
| Nicotinicacid | 1.0 |
| Pyridoxine HCl | 1.0 |
| Thiamine HCl | 1.0 |
| Biotine | 0.1 |
| Ca Pantothenate | 1.0 |
| Hormones: | |
| BAP | 1.0 |
| a NAA | 0.1 |
| Glucose | 20 g/l |
| Sucrose | 20 g/l |
| Bacto-Agar (Difco) | 8.0 g/l |
| pH | 5.8 |

The culture room was regulated at 24° C. day and night with a 16 hour photoperiod. The first ten days the anthers were etiolated in the darkness, followed by three weeks under low light conditions (500 lx). After these weeks the Petri dishes were moved to 1,500 lx.

After eight weeks the anthers were sub-cultivated onto fresh starting medium according to Raquin (1982) (Table 2) and cultivated in a 16 hour photoperiod (1,500 lx). After twelve weeks of cultivation, the first regeneration of callus could be observed. The callus was transferred onto callus and shoot regeneration media as described in Table 3. Every four weeks the anthers were sub-cultivated onto fresh medium of this composition. The first shoot regeneration was established after 4 to 6 months, depending on the genotypes.

TABLE 3

Callus and shoot regeneration media

| | mg/l |
|---|---|
| ½ macro nutriments from M&S-media: | |
| $NH_4NO_3$ | 825 |
| $KNO_3$ | 950 |
| $CaCl_2 * 2 H_2O$ | 220 |
| $MgSO_4 * 7 H_2O$ | 185 |
| $KH_2PO_4$ | 85 |
| Micro nutriments from M&S-media: | |
| $MnSO_4 * H_2O$ | 16.9 |
| $ZnSO_4 * 7 H_2O$ | 8.60 |
| $H_3BO_3$ | 6.20 |
| KJ | 0.83 |
| $Na_2MoO_4 * 2 H_2O$ | 0.25 |
| $CoCl_2 * 6 H_2O$ | 0.025 |
| $CuSO_4 * 5 H_2O$ | 0.025 |
| NaFe-EDTA | 37.5 |
| Vitamins: | |
| Myo-inositol | 100 |
| Nicotinacid | 1 |
| Pyridoxine | 1 |
| Thiamine HCl | 10 |
| Hormones: | |
| Zeatin | 2 |
| IAA | 0.5 |
| Sucrose | 30 g/l |
| Agar | 7.4 g/l |
| pH | 5.8 |

The experiments for anther culture were accomplished from June to October, because during the other months of the year the light intensity is not sufficient. A strong seasonal yield variation could be observed. Experiments which were performed at temperatures higher than 36° C. showed very poor results in callus-regeneration. Cold pre-treatment was given by chilling buds at 6° C. for 5 days. Untreated anthers served as controls.

In the first experimental year four independent experiments were performed. The genotypes were Klemm cultivars, including petunias R 44 ('Klefalec'; European Community Plant Breeder's Right No. EU 8836) (2n=2x), and S 3 ('KLEC01037'; European Community Plant Breeder's Right No. EU 12691) (2n=2x); *Calibrachoa* selections W 002 (2n=4x), W 003 (2n=4x), W 005 (2n=4x), V 172 ('KLEC03074'; European Community Plant Breeder's Right No. EU 14444) (2n=2x) and U 139 (2n=4x); and *C. parviflora* (2n=4x). A total of 920 anthers were cultivated in the first year experiments, which are summarized in Table 4, below, and discussed in detail in the following paragraphs. The ploidy levels of the regenerated shoots were measured by flow-cytometry, and a known standard was used in the analysis as a control.

regenerated plants were tetraploid (2n=4x) and 8 plants even octoploid (2n=8x). In R 44 half of the regenerated shoots were diploid, while the other half were tetraploid. In summary, in *Petunia*, anther culture technique resulted in the successful production of only one plant with reduced ploidy level. This haploid plant died and therefore could not be integrated into further breeding programs. In contrast, many plants showed an increase in ploidy level. This result was unexpected, because the protocol from Raquin (1982), used in these experiments on *Petunia* as a control, was originally described as a method for obtaining *Petunia* plants with reduced ploidy.

The regenerated shoots from *Calibrachoa* genotype W 002 (2n=2x) exhibited numerous mixoploid plants after anther culture. In most cases, however, the ploidy level was diploid, and in one case, tetraploid. The cultivated anthers from *Calibrachoa* genotype W003 did not produce any callus or shoots.

45 anthers of the *Calibrachoa* genotype W 005 (2n=4x) produced 7 calluses. Approximately 3 regenerated shoots were obtained from each callus. Most of these (17) were tetraploid, but 2 shoots exhibited a reduced di-haploid ploidy level (2n=2x), as was expected after anther culture. The di-haploid W 005 plants showed no phenotypic differences from

TABLE 4

Quantity of regenerated plants from anther culture of *Calibrachoa* and *Petunia* and their ploidy level, from the first experimental year (Numbers of plants exhibiting reduced ploidy levels are printed in bold)

| Cultivar or individual anther donor (ploidy level; taxa) | Quantity of anthers | Quantity of anthers producing callus | Plants regenerated from callus and their ploidy level | | | | | | total quantity of regenerated plants per genotype |
|---|---|---|---|---|---|---|---|---|---|
| | | | Haploid | Diploid | Triploid | Tetraploid | Octoploid | Mixoploid | |
| R 44 (2n = 2x; *Petunia*) | 60 | 4 | 0 | 2 | 0 | 2 | 0 | 0 | 4 |
| S 3 (2n = 2x; *Petunia*) | 60 | 16 | 1 | 1 | 0 | 65 | 8 | 0 | 75 |
| W 002 (2n = 2x; *Calibrachoa*) | 60 | 7 | 0 | 12 | 0 | 1 | 0 | 8 | 21 |
| W 003 (2n = 4x; *Calibrachoa*) | 50 | 0 | 0 | 0 | 0 | 0 | 0 | 0 | 0 |
| W 005 (2n = 4x; *Calibrachoa*) | 45 | 7 | 0 | 2 | 0 | 17 | 0 | 0 | 19 |
| V 172 (2n = 2x; *Calibrachoa*) | 425 | 137 | 0 | 66 | 0 | 13 | 0 | 2 | 81 |
| *C. parviflora*. (2n = 4x; *Calibrachoa*) | 220 | 10 | 0 | 238 | 0 | 12 | 0 | 0 | 250 |
| Total amount | 920 | 181 | 1 | 321 | 0 | 110 | 8 | 10 | 450 |

220 anthers from *Calibrachoa parviflora* (2n=4x) were plated on Petri dishes. Callus regeneration was observed on 10 anthers. Shoot regeneration started after 4 months of culture, yielding 1 to 7 shoots per callus. Regeneration followed frequently, so that 250 in vitro shoots were available to transfer to the greenhouse 7 months after the start of the experiment. Flow cytometry analysis showed that 95% of the samples were di-haploid, representing a reduction in ploidy as compared to the tetraploid *Calibrachoa parviflora* genotype.

In *Petunia*, only 7% of the cultivated anthers of genotype R 44 (2n=2x) developed callus, while 27% of the cultivated anthers of S 3 (2n=2x) produced callus. Among 75 *Petunia* S 3 plants which were regenerated from anther culture, one plant had a ploidy level of 2n=2x, the same as the original S 3 genotype, and one plant was haploid. In contrast, 65 of the the original tetraploid genotype W 005 (2n=4x). 96% of their flowers exhibited more than 5 petals per flower. These two di-haploid W 005 plants were integrated into the breeding programs described herein above.

Cultivars of di-haploid *Calibrachoa parviflora* and di-haploid *Calibrachoa* genotype W 005 produced by anther culture were used in further breeding activities to obtain diploid progeny that show double flowering types. The breeding program included outcrossing to increase genetic diversity and to obtain a broader range of flower colors in the seedling population.

The genotypes used for the second year experiments were Klemm cultivars, including *Petunia* S 3 (2n=2x) and *Calibrachoa* W 005 (2n=4x), X 436 (2n=4x) and X 437, as well as *Calibrachoa parviflora* (2n=4x). All tetraploid *Calibrachoa* genotypes included in the experiments showed more than 5 petals per flower (double types). Nine independent experiments were accomplished in the second year of experiments. The results of the second year experiments are summarized in Table 5.

level is much higher. With anther culture, layers of the cell wall (organogenic cells) can regenerate to callus and plant shoots that due to their origin are not haploid or di-haploid, but diploid or tetraploid, respectively.

TABLE 5

Quantity of regenerated plants from anther culture of *Calibrachoa* and *Petunia* and their ploidy level from the second experimental year (Numbers of plants exhibiting reduced ploidy levels are printed in bold)

| Cultivar or individual anther donor (ploidy level; taxa) | Quantity of anthers | Quantity of regenerated callus | Haploid | Diploid | Triploid | Tetraploid | Octoploid | Mixoploid | total quantity of regenerated plants per genotype |
|---|---|---|---|---|---|---|---|---|---|
| S 3 (2n = 2x; *Petunia*) | 150 | 0 | 0 | 0 | 0 | 0 | 0 | 0 | 0 |
| W 005 (2n = 4x; *Calibrachoa*) | 1482 | 381 | 0 | 0 | 0 | 83 | 0 | 0 | 83 |
| W 014 (2n = 4x; *Calibrachoa*) | 405 | 140 | 0 | 0 | 0 | 7 | 0 | 0 | 7 |
| X 436 (2n = 4x; *Calibrachoa*) | 26 | 0 | 0 | 0 | 0 | 0 | 0 | 0 | 0 |
| X 437 (2n = 4x; *Calibrachoa*) | 34 | 0 | 0 | 0 | 0 | 0 | 0 | 0 | 0 |
| *C. parviflora* (2n = 4x; *Calibrachoa*) | 350 | 6 | 0 | 36 | 0 | 0 | 0 | 0 | 36 |
| Total amount | 2607 | 534 | 0 | 36 | 0 | 90 | 0 | 0 | 126 |

All regenerated shoots of *Calibrachoa* W 005 (2n=4x) and *Calibrachoa* W 014 (2n=4x) were analyzed by flow cytometry and proved to be tetraploid after anther culture. From 350 anthers of *Calibrachoa parviflora* (2n=4x) only 1.7% regenerated callus. About 6 shoots regenerated from each callus and 100% of the shoots were proved to be di-haploid. Anthers from *Calibrachoa* varieties X 436 and X 437 did not regenerate any callus or shoots, nor did anthers from the *Petunia* variety S 3.

The genotypes for the third experimental year were *Calibrachoa* seedlings from the current progeny: CA 05 0605 (2n=4x), CA 05 0611 (2n=4x), CA 05 0620 (2n=4x), CA 05 0634 (2n=3x), CA 05 0636 (2n=4x), CA 05 0638 (2n=4x), CA 05 0639 (2n=2x), CA 05 0661 (2n=4x), CA 05 0662 (2n=4x) and CA 05 0664 (2n=3x/4x). All the involved genotypes showed double flower types. CA 05 0639 is a seedling from an anther culture derived from the di-haploid W 005. Most of the flowers of the genotype CA 05 0639 have approximately 8 to 10 petals. The anthers formed callus in culture, and first shoot regeneration has been observed.

Figure 11:
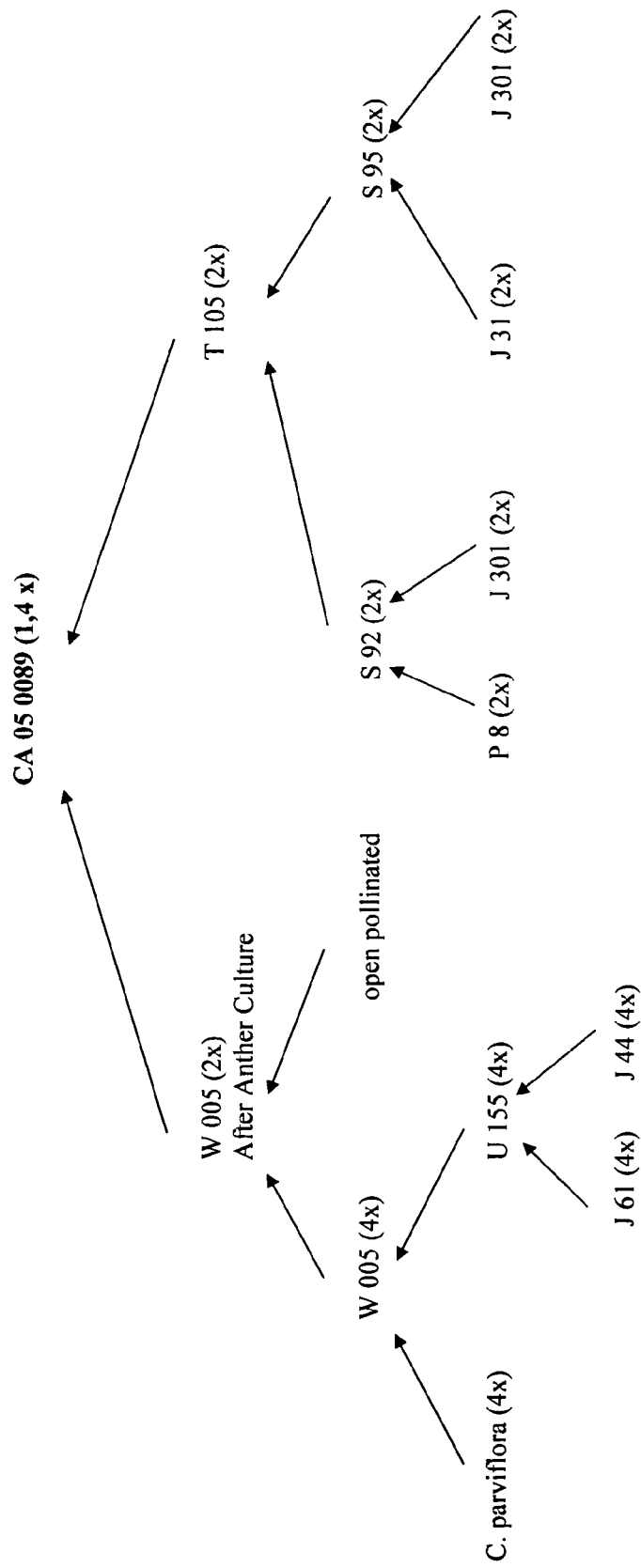
FIG. 11 shows the genealogy of double-type cultivar CA 05 0089 (2n=1.4x); received from a cross-combination of anther culture derived diploid W 005 and a diploid Klemm cultivar T 105.
Figure 12:
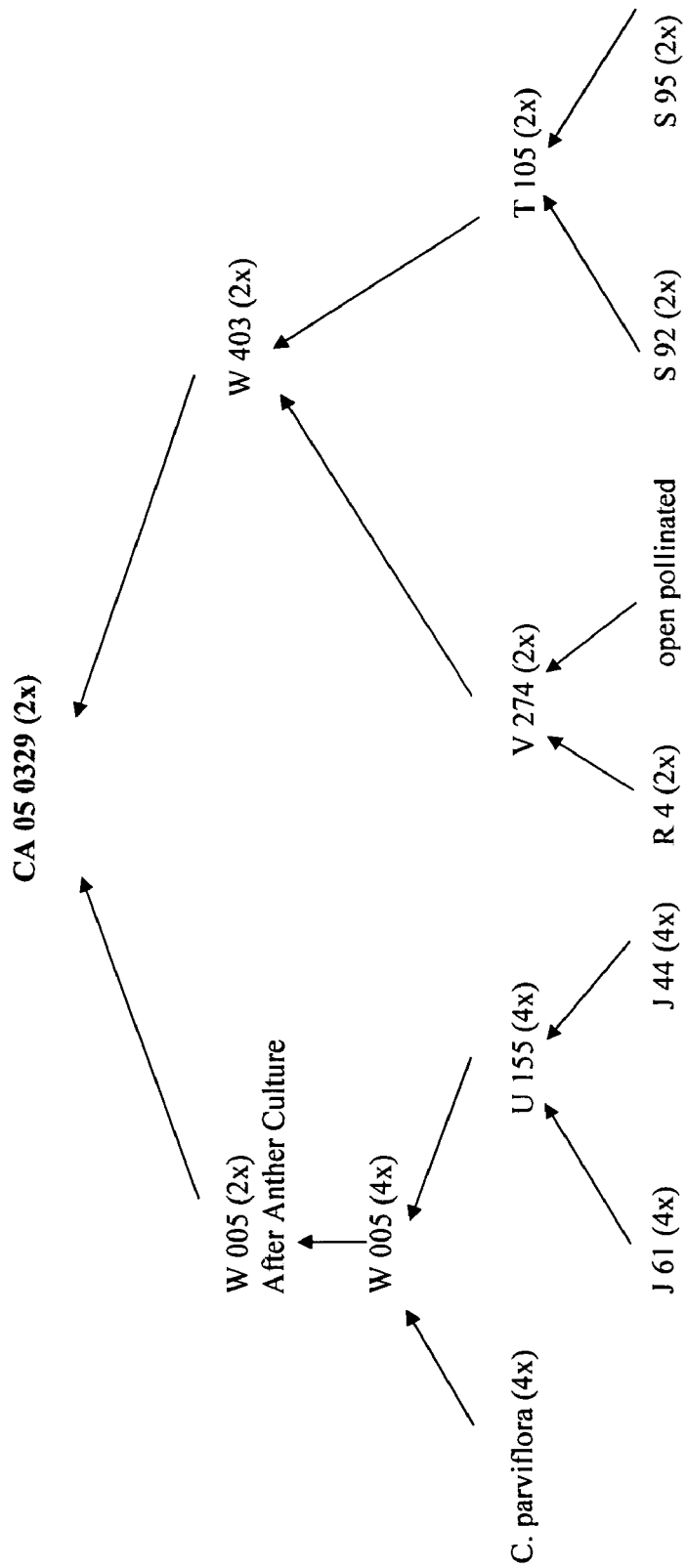
FIG. 12 shows the genealogy of double-type cultivar CA 05 0329 (2n=2x) received from a cross-combination of anther culture derived diploid W 005 and a diploid Klemm cultivar W 403.
Figure 13:
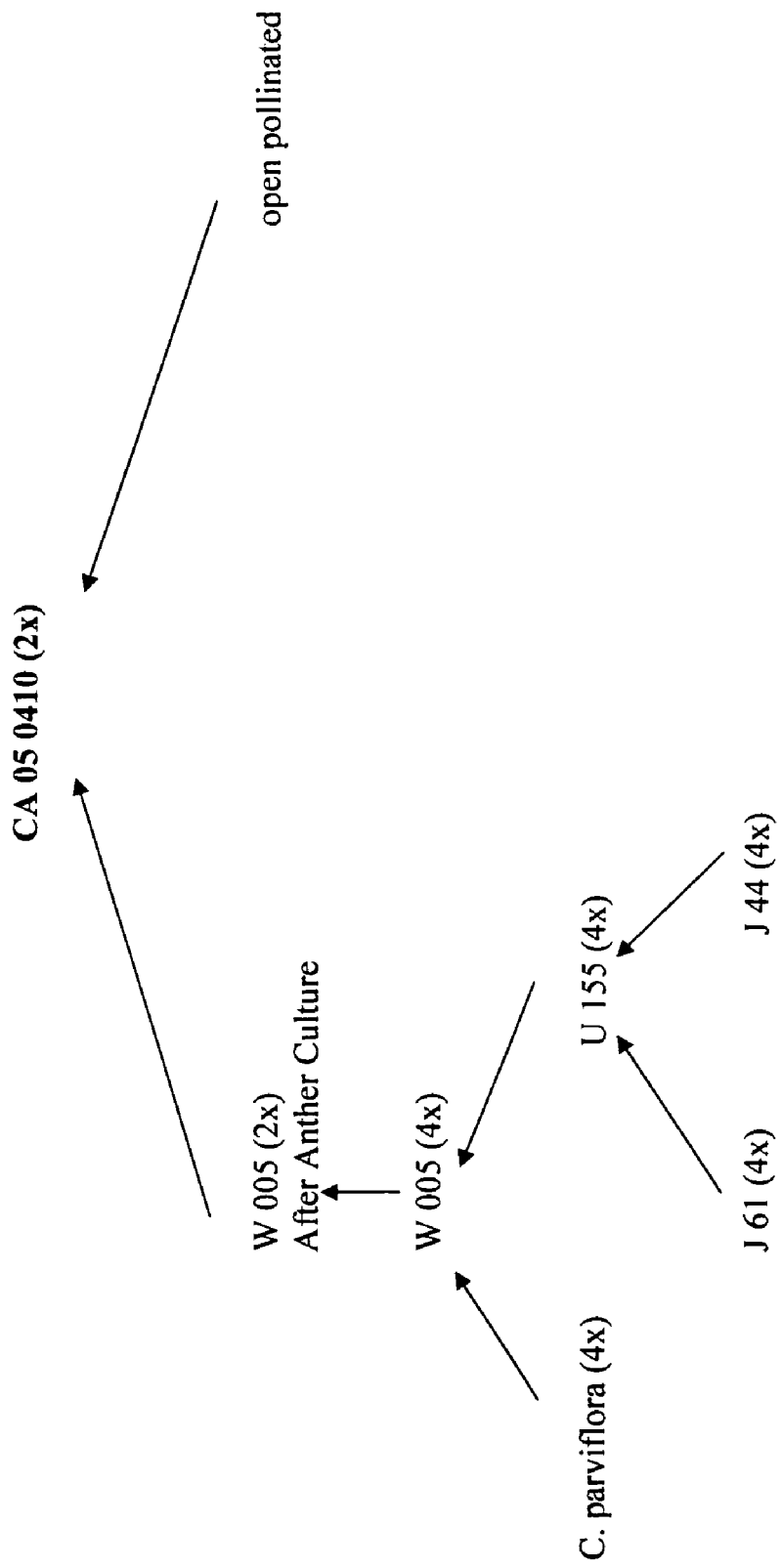
FIG. 13 shows the genealogy of double-type cultivar CA 05 0410 (2n=2x) received from a open pollinated anther culture derived diploid W 005.
Figure 14:
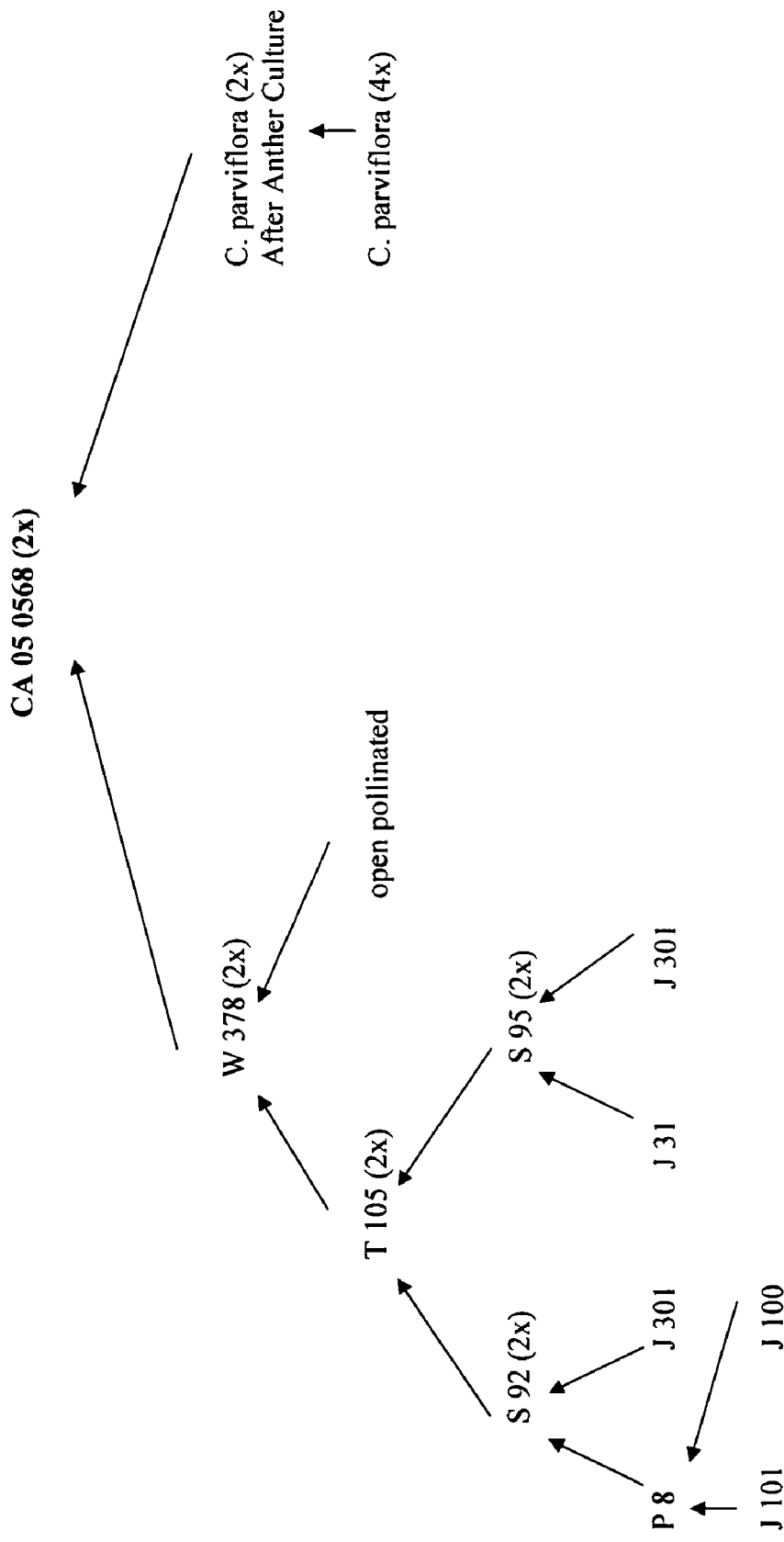
FIG. 14 shows the genealogy of double-type cultivar CA 05 0568 (2n=2x) received from a cross-combination of anther culture derived diploid *C. parviflora* and a diploid Klemm cultivar W 378.
Figure 15:
FIG. 15 is a color photograph of a double flower *Calibrachoa* plant produced by the method of the invention.

The genealogies shown in FIGS. 11 to 14 of double-flowering *Calibrachoa* show the results of crossings with anther culture derived diploid double-flowering *Calibrachoa* genotypes.

The genotypes of *Calibrachoa* and *Petunia* used in the anther culture experiments described above include inbred lines, F1 hybrids, backcross progeny, and genotypes which are highly heterozygous. Only certain genotypes of anther donor *Calibrachoa* or *Petunia* plants have produced plantlets from cultured anthers. Genotype differences in anther culture results among *Calibrachoa* species and varieties, as well as between varieties of *Petunia*, have been noted.

It is also expected that the technique of microspore culture will result in the generation of haploid or di-haploid plants from a single microspore, and it is further expected that the likelihood of obtaining plants exhibiting a reduced ploidy level is much higher. With anther culture, layers of the cell wall (organogenic cells) can regenerate to callus and plant shoots that due to their origin are not haploid or di-haploid, but diploid or tetraploid, respectively.

It is expected that any *Calibrachoa* cultivar or species can be used to produce haploid, di-haploid plantlets through anther or microspore culture. All di-haploid *Calibrachoa* varieties and *Calibrachoa parviflora* plants thus far tested have been found to be stable through asexual propagation.

Mutation Breeding to Induce Double Flowering Types Within the Genus *Calibrachoa*:

Due to the fact that the double flowering trait may be inherited by a single gene it is expected that double flowering plants will emerge as a result of a mutation of the respective gene. The mutation can arise spontaneously or can be induced by treatment of the plant material with a mutagenic agent such as Gamma-irradiation. The resulting mutated trait might be inherited dominantly or recessively. Whereas dominantly inherited traits are visible within the first generation, recessively inherited traits do not become visible before all alleles per locus are carrying the same mutation, which can be achieved by self-pollination of the original mutant.

For mutation treatment the donor plants are grown at 16° C. to 20° C. day and night temperature. They are watered with a solution containing 20% nitrogen, 5% potassium, 10% phosphorus and 2% magnesia. From these plants, cuttings exhibiting at least 2 mature leaf pairs are taken and rooted in paperpots (2.5 cm diameter, pH 4.3). After about 3 weeks the rooted cuttings are treated with 30 Gy Gamma-irradiation. The cuttings so treated are planted into standard pots, grown and cultivated as described for the donor plants. Alternatively to cuttings from greenhouse grown plants, in-vitro-shoots which have been cultivated for 3 weeks on MS-medium without growth regulators can be used for irradiation treatment.

As soon as the irradiated plants start to flower crosses are performed. Under European light conditions, crosses can be made from May until September. In order to accumulate the mutated genes the flowers must be self pollinated. However, because *Calibrachoa* has a self-incompatibility system, this barrier must be overcome in order to accomplish self-pollination. For this purpose, young flower buds to be used as the female parent are emasculated as soon as the buds are showing color. After emasculation, and for the 2 days following emasculation, the stigmas from the emasculated flowers are pollinated. In order to enhance the frequency of combining genes which are mutated for the same alleles, the flower to be used as the male parent should originate from the same branch as the female flower. Crosses are performed over a period of 3 months using all available flowers for self-pollination. The further proceeding is as described herein above for interspecific hybridization. The resulting progeny are scored for plants exhibiting flowers with more than 5 petals.

The double-type flower characteristic can be predictably bred into diverse single-type or double-type *Calibrachoa* genetic backgrounds using the methods described hereinabove. Double-flowering *Calibrachoa* cultivars can be predictably selected in which substantially all the flowers produced are double-type. The degree of doubleness per flower or plant can be predictably increased by means of recurrent selection. The double-type characteristic can be predictably combined with other desirable *Calibrachoa* characteristics to produce commercially acceptable cultivars that can be stably reproduced by asexual propagation. The pool of *Calibrachoa* cultivars available for breeding can be increased through the use of anther culture techniques to reduce ploidy in cultivars having desirable traits. It is also anticipated that double flowering plants will emerge as a result of the mutation of a double flowering gene in *Calibrachoa*. The mutation can arise spontaneously, or can be induced by treatment of the plant material with a mutagenic agent.

DEPOSIT INFORMATION

A deposit of a sample of representative seed of a *Calibrachoa* plant having at least one flower with more than 5 petals is disclosed above and recited in the appended claims has been made with the National Collections of Industrial, Food and Marine Bacteria (NCIMB), 23 St Machar Drive, Aberdeen, Scotland, AB24 3RY, United Kingdom. The date of deposit was Jan. 13, 2010. The deposit of 2,500 seeds was taken from the same deposit maintained by KLEMM & SOHN GMBH & CO. KG since prior to the filing date of this application. All restrictions upon the deposit will be removed upon the granting of a patent, and the deposit is intended to meet all of the requirements of 37 C.F.R. 1.801-1.809. The NCIMB Accession Number is 41691. The deposit will be maintained in the depository for a period of 30 years, or 5 years after the last request, or for the effective life of the patent, whichever is longer, and will be replaced as necessary during that period.

The invention claimed is:

1. A *Calibrachoa* plant having at least one flower with more than five petals, wherein a sample of representative seed of a *Calibrachoa* plant having at least one flower having more than five petals is deposited under NCIMB Accession No. 41691.

2. Seed of the *Calibrachoa* plant of claim 1.

3. A *Calibrachoa* plant, or a part thereof, produced from growing the seed of claim 2.

4. The seed of claim 2, wherein the seed deposit is comprised of a mixture of seeds comprised of *Calibrachoa* varieties W002, W003, W005 and W006.

5. A tissue culture of cells produced from the plant of claim 1, wherein said cells of the tissue culture are produced from a plant part selected from the group consisting of seed, leaf, pollen, embryo, cotyledon, hypocotyl, meristematic cell, root, root tip, pistil, anther, flower, stem, and petiole.

6. A *Calibrachoa* plant regenerated from said tissue culture of claim 5.

7. A method for producing a hybrid *Calibrachoa* seed containing at least one flower with more than five petals comprising crossing a first parent *Calibrachoa* plant with a second parent plant and harvesting the resultant hybrid *Calibrachoa* seed, wherein said first parent *Calibrachoa* plant is the *Calibrachoa* plant of claim 3.

8. A method for breeding a *Calibrachoa* plant having at least one flower with more than five petals, comprising the steps of:
   selecting a male parent and a female parent to produce first generation plants,
   wherein the male parent or the female parent is the *Calibrachoa* plant of claim 1; and
   selecting from the first generation plants a plant having at least one flower with more than five petals.

9. A *Calibrachoa* plant produced by the method of claim 8.

10. The method of claim 8, wherein the male parent *Calibrachoa* plant or the female parent *Calibrachoa* plant is a tetraploid *Calibrachoa parviflora*.

11. The method of claim 8, wherein one of the selected parents is a diploid *Calibrachoa parviflora*.

12. The method of claim 8, wherein one of the selected parents is a diploid *Calibrachoa parviflora* plant obtained from anther culture of a tetraploid *Calibrachoa parviflora* plant and the progenies thereof.

* * * * *